United States Patent [19]

De Pous

[11] Patent Number: 4,947,125

[45] Date of Patent: Aug. 7, 1990

[54] METHOD AND DEVICE FOR DETERMINING OXYGEN IN GASES

[75] Inventor: Olivier De Pous, Chene-Bougeries, Switzerland

[73] Assignee: Honda Motor Co., Ltd., Tokyo, Japan

[21] Appl. No.: 908,714

[22] Filed: Sep. 18, 1986

[30] Foreign Application Priority Data

Oct. 1, 1985 [EP] European Pat. Off. ......... 85810452.4

[51] Int. Cl.$^5$ ............................................. G01N 27/62
[52] U.S. Cl. ..................................... 324/459; 324/715; 204/424
[58] Field of Search ............... 204/1 T, 424, 425, 426, 204/427, 428, 429; 324/71.5, 459, 461

[56] References Cited

U.S. PATENT DOCUMENTS

| | | | |
|---|---|---|---|
| 3,691,023 | 9/1972 | Ruka et al. | 204/1 T |
| 3,843,489 | 10/1974 | Sandler | 204/1 T |
| 3,883,408 | 5/1975 | Kim et al. | 204/424 |
| 3,989,612 | 11/1976 | Tien | 204/182.1 |
| 4,119,512 | 10/1978 | Inoue et al. | 204/429 |
| 4,121,988 | 10/1978 | Sano et al. | 204/429 |
| 4,145,272 | 3/1979 | Nakamura et al. | 204/412 |
| 4,151,060 | 4/1979 | Isenberg | 204/428 |
| 4,158,166 | 6/1979 | Isenberg | 204/1 S |
| 4,189,355 | 2/1980 | Fujishor et al. | 204/1 S |
| 4,199,424 | 4/1980 | Teitelbaum | 204/428 |
| 4,230,555 | 10/1980 | Sano et al. | 204/427 |
| 4,394,222 | 7/1983 | Rohr | 204/1 S |
| 4,402,820 | 9/1983 | Sano et al. | 204/429 |
| 4,407,704 | 10/1983 | Mase et al. | 204/1 S |
| 4,502,939 | 3/1985 | Holfelder et al. | 204/1 S |

FOREIGN PATENT DOCUMENTS

2358655 2/1978 France .

Primary Examiner—A. D. Pellinen
Assistant Examiner—Jeffrey A. Gaffin
Attorney, Agent, or Firm—Cushman, Darby & Cushman

[57] ABSTRACT

This device provides an electric signal linearly dependent on the oxygen content of a gas without the need of a reference gas; it is constituted by a solid electrolyte substrate (3) coated with two separate electrodes (1,2) connected to the terminals of an electric voltage source. In the presence of a gas of which the content of oxygen must be measured and when a given voltage is applied between the two electrodes (1,2), oxygen molecules are ionized in the region of the electrolyte close to the cathode (1). The current which flows between the two electrodes (1,2) constitutes the measuring electric signal provided by the sensor.

9 Claims, 3 Drawing Sheets

METHOD AND DEVICE FOR DETERMINING OXYGEN IN GASES

The present invention concerns a method and a device for measuring oxygen in a gas of unknown composition. This method relies on measuring the electric current flowing across a dry electrolytic cell containing a body of solid electrolyte under an electric DC field, said current originating from the ionization of elemental oxygen in the unknown gas to which said electrolyte body is exposed under the influence of said electric field. Such an electrolytic cell comprises a body of solid electrolyte subjected to an electric DC field provided by at least two electrodes, a cathode and an anode in contact with the electrolyte. The current is produced by the migration through the electrolyte of $O^2$ ions resulting from the ionization of elemental oxygen from the gas in contact with the electrolyte in the vicinity of the cathode.

Among the known means for measuring the quantity of oxygen contained in a gasous mixture, devices exist which are formed by a solid electrolyte membrane on each side of which a porous electrode is fixed. This membrane separates the gaseous mixture to be analysed from a reference gas. If the oxygen content of this mixture is different from that of the reference gas, an electric potential is generated which is a logarithmic function of the oxygen concentrations difference in the two gases. Measuring this potential and knowing the oxygen content of the reference gas makes it possible to determine the oxygen content of the gaseous mixture. In this kind of determination, it is generally accepted to provide a contact area between the gas mixture, the electrolyte and the cathode, as wide as possible; consequently the use of porous cathodes permeable to the gas is commonly recommended.

A method of manufacturing porous electrodes used for this type of sensor is disclosed in U.S. Pat. No. 4,372,824. In this method, an electrode is placed on a solid electrolyte and is then subjected to a heat treatment capable of increasing its porosity. The aim of this treatment is to favour the penetration of the oxygen into the solid electrolyte so as to improve the sensitivity of the sensor.

The logarithmic behaviour of these sensors makes them very efficient for measuring small oxygen concentrations (less than 0.5%) which pertains, for instance, to exhaust gases resulting from the combustion of an air/fuel mixture of ratio close to stoichiometry. They are, however, not well adapted for determining higher concentrations of oxygen and furthermore, the response of such sensors remains largely dependent on temperature.

In order to remove these disadvantages, sensors defined as the "oxygen pump" type have been proposed. These sensors are formed, as mentioned above, by a solid electrolyte membrane the opposite sides of which are covered with porous electrodes. The originality of this type of sensor lies in the fact that the electrodes are connected to a source of electric power which, by virtue of the DC electric field it provides, promotes the formation of oxygen $O^{--}$ at the cathode and causes the migration thereof across the membrane. In order to be practically operative under high oxygen concentration conditions, the cathode is coated with an element designed to limit the flow of oxygen-containing gas capable of migrating across this membrane.

This element may be formed by a porous ceramic layer integral with said cathode such as disclosed in patent application published before examination, JP 57-48648, where the porosity of the ceramic layer was chosen of a degree such that, in normal conditions of use of the sensor, this layer limits in a well-defined manner the flow of gas capable of coming into contact with the cathode. Therefore, the flow of molecular oxygen be transformed into ions that will migrate through the solid electrolyte is proportional to the difference in the oxygen partial pressures on both sides of the membrane. Then, the value of the electric current that flows across the electrolyte as the result of the migration of the oxygen ions is, therefore, a function of the oxygen content of the gas penetrating into the ceramic layer.

Furthermore, an element for limiting the oxygen flow having the form of a capsule comprising a calibrated orifice is known from patent application JP 52-72286 published before examination.

In order to obtain good performance from this type of sensor, there is advantage in having electrodes whose porosity is very high so as to favour as much as possible the penetration of the oxygen into the solid electrolyte.

Sensors of the "oxygen pump" type using this type of limitation of the flow of oxygen-containing gas have various major drawbacks. The solid particles possibly suspended in the gaseous mixture to be analyzed tend to plug the pores of the ceramic layer or to alter the cross-section of the capillary pores, which will restrict the flow of oxygen through the sensor so that the behaviour thereof may change with time. Moreover, the response time of such sensors is generally very long and therefore they are not well-suited when it is necessary to measure rapid variations in the oxygen content of a gas. This excessive response time is mainly due to the low rate of diffusion of the gaseous flow in the element which limits the flow of oxygen-containing gas through the probe.

Patent CH 478.463 discloses an electrode which can be used in a solid electrolyte fuel cell. This electrode is formed by an underlayer consisting of a sintered electron and ion conductive ceramic material, which is applied to a solid electrolyte substrate such as zirconia and by a porous layer having good electronic conductivity and integral with said underlayer. This electrode is designed to enable a large quantity of oxygen to pass into the solid electrolyte.

The prior art also comprises DE-A-1.954.663 which discloses an oxygen measuring probe comprising an anode and a cathode whose surface is largely in electrical contact with a solid electrolyte body in a manner such that one electrode can be brought into contact with a reference gas containing oxygen while the other electrode can be contacted with an oxygen containing gas to be analyzed; and the electrodes are connected to a voltage source via an ammeter for measuring the current flowing between the electrodes and the electrolyte body. The electrodes are porous and would not be operative unless this is so.

DE-A-2.906.459 discloses a probe for measuring oxygen in gases which also comports a solid electrolyte conductive of $O^{--}$ ions and, in electrical contact therewith, two electrodes, a measuring electrode and a reference electrode in contact with oxygen at a (partial) pressure of reference. This oxygen at a reference partial gaseous pressure is provided by dynamic means, i.e. by controlling the amount of an oxygen containing gas (air) coming into contact with, or leaving the reference electrode and by passing it through a porous structure that physically isolates the reference electrode from the outside. This porous structure can consist of either the electrode itself (which can be made porous to gases in molecular form) or by shield applied over the reference electrode (see the drawing, FIGS. 1 to 5).

DE-A-3.33.783 discloses an apparatus for measuring the concentration of oxygen in a gas, namely in the exhaust gases of an internal combustion engine. One element of this apparatus is a detecting probe illustrated on FIG. 1 and described at pages 10–12. This probe consists essentially of a layer of solid electrolyte and two electrodes 4 and 5, one of them (4) in contact with the exhaust gases and the other (5) with the atmosphere (reference) through a porous sheet 3. Both the electrodes have a porous structure.

Document FR-A-2.358.655 discloses a device for measuring oxygen in gases including free oxygen (molecular oxygen) and bound oxygen, i.e. oxygen as a moiety in gaseous compounds such as $CO_2$, $CO$, $NO_2$, etc. One embodiment of such device is illustrated on FIG. 1 and described at pages 7 and 8. It comprises a solid electrolyte 12 conductive of $O^{--}$ ions, a measuring electrode 13 and a counter-electrode 14. When a voltage sufficient to ensure the circulation of oxygen ions through the electrolyte is applied to the electrodes and in the presence of an oxygen containing gas around electrode 13, a current proportional to the oxygen content of the gas under test will circulate. The electrode may be porous but not necessarily so (see page 5, line 21). Further, according to the drawing, there exists, like in the aforediscussed embodiment of DE-A-2.906.459, areas of the electrolyte uncovered by the test electrode but still in contact with the gas under test. This implies the existence of boundary lines at the junction of the electrode with the electrolyte, the latter extending freely on both sides of the electrode and allowing the formation of an $O^{--}$ ion current flow.

Document U.S. Pat. No. 4,372,824 discloses the manufacture of oxygen sensors composed of a solid electrolyte structure coated on each side with an electrode permeable to oxygen containing gases.

At least one of these electrodes (see the Example, col. 6) consists of a platinum layer about 1 μm thick with holes about 5–6 μm average diameter therein for allowing the test gas to get across the electrode and come into contact with the electrolyte.

It thus appears that all the embodiments of the prior art in which an electrolytic cell is used that comprises a dry solid electrolyte body exposed to the oxygen containing gas to be determined rely on the additional presence of a reference gas containing a known amount of oxygen and/or on the use of electrodes of high porosity. No embodiment appears to exist yet in which an dry electrolytic probe cell is used that it includes a solid electrolyte body and electrodes in contact therewith in which the conduction parameters, i.e. the charge transport properties of this electrolyte in a region thereof in the vicinity of the electrodes are determinant regarding the measuring of the oxygen content of a gas in contact with said region of the electrolyte.

The method of the present invention remedies this situation; this method can be implemented by a device defined in the appended claims which involves a sensor capable of generating an electric signal linearly dependent on the oxygen content of a gaseous mixture without the need of a reference gas. Moreover, since the presence of a reference gas can be avoided, the electrolyte no longer needs to act as a separator between the test and the reference gases. Therefore, in some embodiments of the present sensor, both anode and cathode are placed side by side, on a same even face of the electrolyte body; in this case, the electrolyte body is preferably evenly shaped, e.g. plate-like. In one particular embodiment of the sensor, the solid electrolyte also constitutes the supporting base-plate of the sensor, which architecture enables to markedly decrease the bulk of the sensor cell. This reduction of the volume of the electrolyte and a flat slab-like structure are advantageous because they help reducing the cost of the material used to manufacture the sensor and because the electrolyte can be brought to its operating temperature more rapidly and with less energy than in the prior art embodiments.

The annexed drawing schematically illustrates several embodiments of the device according to the invention as well as its operation.

FIGS. 1 to 10 are schematic perspective and cross-sectional views illustrating particular embodiments of the device according to the invention.

FIGS. 11 and 12 are schematic representations of installations embodying the device according to the invention.

Figure 1:
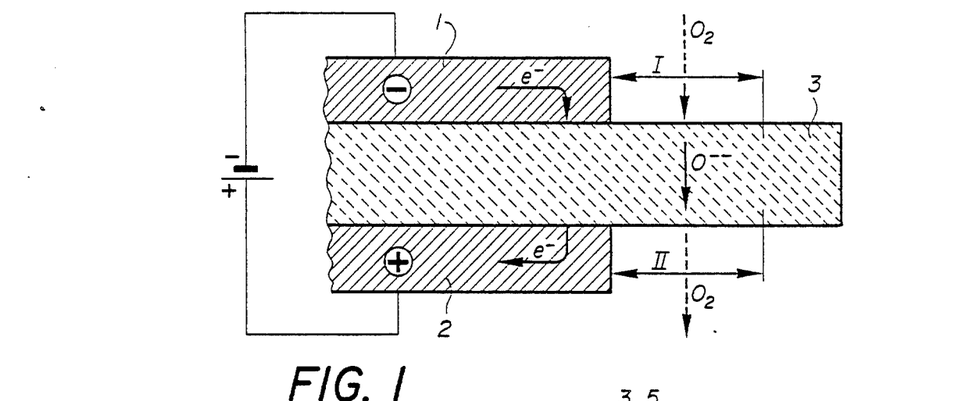
FIG. 1 shows a cross-sectional view of electrodes having a continuous cathode/electrolyte junction boundary.

The device represented on FIG. 1 comprises a cathode 1 and an anode 2. These electrodes are integral with a substrate body 3, made of a solid zirconia electrolyte conductive of oxygen ions but impervious to oxygen gas, to be exposed to a gaseous mixture whose oxygen content is not known. Under the effect of the DC electrical field applied to the electrodes, there appears in the neighborhood of the cathode 1 a contact zone I on the surface of the electrolyte on which the oxygen is ionized ($O_2 \rightarrow 2O^{--}$). Under the effect of the electric field set up between the electrodes, the $O^{--}$ ions migrate in the electrolyte towards the anode 2 where they are neutralized in a contact region or zone II of the electrolyte by losing the negative charges, whereby they reconvert to molecular oxygen, the latter being thereafter returned to the ambient atmosphere.

This ionic circulation therefore generates between electrodes 1 and 2 an electrical current which can be measured by usual means.

As already mentioned above, in the prior art sensor cells, the current between the electrodes depends on the following factors: The rate of oxygen ionization in the neighorhood of the cathode, the oxygen ion migration flow in the solid electrolyte body and the rate of oxygen release at the anode.

In the present invention the arrangement of electrodes and electrolyte, i.e. sensor geometry, is such that the current in the cell only depends on the rate of oxygen ionization in the vicinity of the cathode. It has been recognized that the ionization of oxygen is rate determinant when the areas of zones I and II are about equivalent, as the current is limited by the charge transfer properties of the solid electrolyte in the vicinity of the cathode. When the electrolyte is a purely ionic conductor (zirconia stabilized with 10% of yttrium oxide, the density of charges formed near electrode 1 is small: the development of zone I in the vicinity of the cathode 1 is consequently relatively narrow even if the voltage applied between electrodes 1 and 2 is large. In contrast, in the case where the electrolyte has a mixed conductivity, that is, when it is simultaneously an electronic and ionic conductor, (for instance with stabilized zirconia doped with cerium or uranium oxides), the density of charges appearing near cathode 1 is larger and zone I becomes therefore wider.

It should be noted that the overall ionic cross-resistance per unit of area of a solid electrolyte (which decreases exponentially with temperature) is inversely proportional to the distance of migration of the ions in the electrolyte. Thus, in case the electrodes are located on opposite sides of a slab of solid electrolyte (like in the cae of the embodiment of FIG. 1), the thickness thereof must not exceed a certain value to ensure that the ionic resistance does not exceed $10^3$ ohms per centimeter of the length of the cathode/electrolyte junction boundary line in region I. Further, the electric field, as defined by the voltage applied to the cathode, can be adjusted within the given range to get optimal sensitivity and, if required, to compensate for the temperature effect. Indeed, raising the temperature will decrease the internal resistance of the electrolyte. In the practice of this invention, it has been found that operating at temperatures where the internal resistance of the electrolyte to the flow of $O^{-2}$ ions becomes about a tenth or less of the resistance associated with $O_2$ ionization is suitable. A range of temperature to reach such conditions is about 500°–900° C. Also keeping the electrodes at short distance from each other will decrease the inter-electrode resistance.

A device constructed and operating under the aforementioned criteria generates a signal representative of the oxygen content of a gaseous mixture to be analyzed and this signal can be made linearly dependent on said oxygen content.

For this, the geometry of the electrodes relative to the electrolyte should be adapted to ensure that the controlling effect of zone I predominates over that of zone II. Such conditions are met when the rate of conversion of oxygen gas into ionic oxygen is markedly below the maximum ionic flow capacity of the electrolyte between the electrodes and the maximum output of oxygen release at the anode. Thus, zone II should be, operatively speaking, at least as "wide" as zone I and, preferably, wider.

Figure 2:
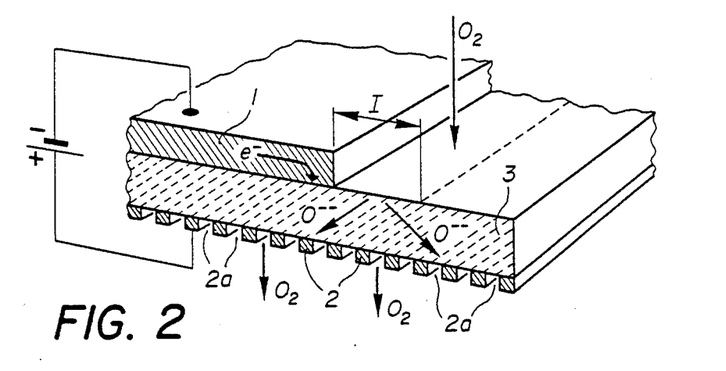
FIG. 2 shows a perspective and cross-sectional view of electrodes having a porous anode/electrolyte junction boundary and a straight cathode/electrolyte boundary.
Figure 3:
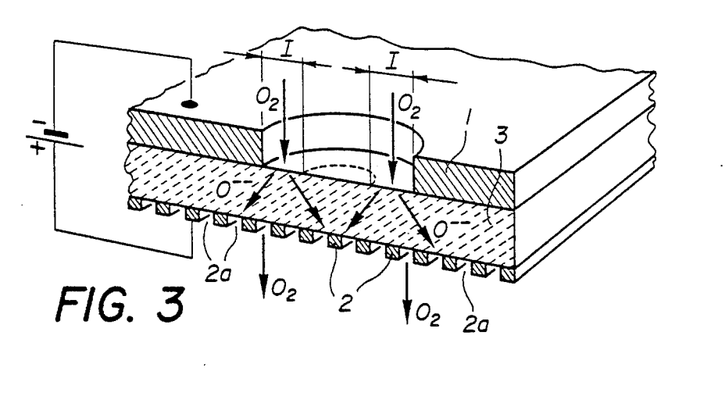
FIG. 3 shows a perspective and cross-sectional view of an electrode arrangement having a porous anode/electrolyte junction boundary and a circular cathode/electrolyte boundry.
Figure 4:
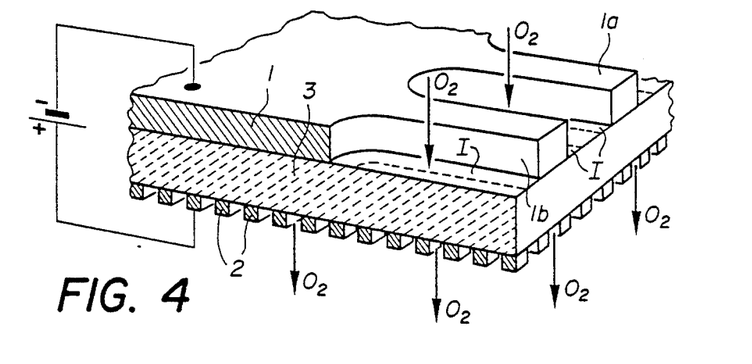
FIG. 4 shows a perspective and cross-sectional view of electrodes having a porous anode/electrolyte junction boundary and a cathode/electrolyte boundary having yet another shape.

In order to widen Zone II relative to zone I, a cell architecture of the type exemplified in FIG. 2 is suitable. The anode 2 is made of a porous electroconductive material, while cathode 1 is plain. Zone II corresponds therefore to the total of the area of the electrolyte not covered by the anode, i.e. to pores 2a in the anode. In the embodiment of FIG. 1, zone I is defined by a continous cathode/electrolyte junction boundary. In the embodiments of FIGS. 2, 3 and 4, zone II is defined by a plurality of unconnected pore boundary lines. In the present application, the term "porous" refers to openings in the anode; these openings are of a size not exceeding 10 $\mu$m. Openings of a size definively above 10 $\mu$m and, preferably above 100 $\mu$m, do not refer to a porous structure, in the present sense but rather to a structure with "holes" or discontinuities. In this connection, it should be remarked that for the efficient performing of the present method and apparatus, the size of the holes in the cathode or the distance between facing edges in a jig-saw cut electrode should not be lower than about two or three times the width of the cathode-electrolyte boundary region (zone I) corresponding to the highest oxygen concentration to be measured (about 20-15 $\mu$m). In contrast, regarding the anode it is preferred to use a material with a fine pore structure.

As we have seen already, in order to get correct results, the current between the two electrodes should not be under limiting control from the rate of migration of oxygen ions ($O^{--}$) in the solid electrolyte.

This is achieved in the present system by keeping the internal resistance low, i.e. by maintaining the sensor at a temperature of about 500° to 900° C. and keeping the distance between the electrodes short (lower than 300 microns, preferably 100–300 $\mu$m). Also, increasing the length of the cathode/electrolyte junction boundary line will decrease the effective path resistance between the electrodes. It has thus been found that the ohmic resistance in the solid electrolyte body between the electrodes must be lower than $10^3$ Ohm per centimeter of the cathode/electrolyte junction boundary line in zone I, in which case, this internal resistance becomes negligible relative to the current limiting parameters.

Assuming that these conditions are fulfilled, the quantity of oxygen ions formed per unit of time depends on the extent of zone I available for being exposed to the gas.

Figure 5:
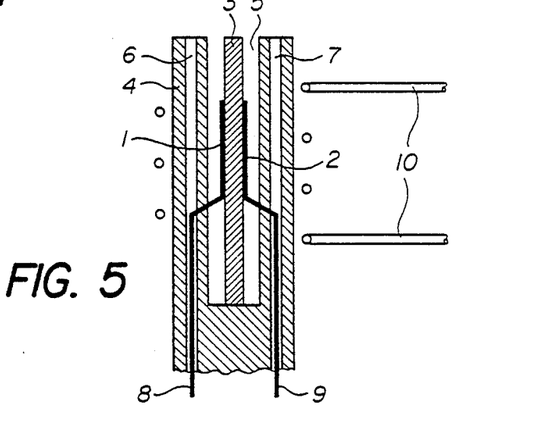
FIG. 5 shows a cross-sectional view of a sensor involving the structure of FIG. 1 of this invention.

The embodiment represented on FIG. 3 differs from that of FIG. 2 by the shape of the cathode-electrolyte boundary line; as can be seen from the drawing, this line is semi-circular while it was straight in the embodiment of FIG. 2. Actually, FIG. 3 can consist of a cross-sectioned representation of a fully circular cathode-electrolyte boundary area obtained by providing a circular opening in the cathode 1 applied over the electrolyte body 3. For proper operation of the present sensor the size of said opening should be at least 100 micrometers in diameter while the size of the openings in the anode (pores) can be 10 micrometers or less. For proper operation of the present process and device, the openings in the cathode should preferably be about one order of magnitude greater than the size of the pores in the anode. Naturally the openings in the cathode can be of any shape; square, triangular, elongated, etc. . . An embodiment with a differently shaped cathode is shown in FIG. 4. In this figure the dotted line defines approximately the limits of the cathode-electrolyte boundary region and the length of this boundary (zone I) is that length to be considered when applying the required voltage according to the conditions exposed in claim 1. In general, the width of this boundary region is variable and depends on the concentration of oxygen in the gas to be analyzed; with the highest oxygen concentrations involved in the present measurements, i.e. about 20–30% v/v this width does not exceed about 50–100 micrometers. So in FIG. 4, the two protruding jig-saw cut portions $1a$ and $1b$ of the cathode should be separated by about two to three times the width of the boundary region, i.e. about 100–150 $\mu$m or more. However, simultaneously, this distance should be kept short otherwise the cathode would become oversized. One embodiment of a sensor according to the invention and involving the structure disclosed on FIG. 1 is illustrated on FIG. 5. This sensor comprises an insulative supporting substrate 4 comprising a recess 5 with a rectangular plate 3 made of a solid ionic conductive electrolyte, such as for instance stabilized $ZrO_2$; substrate 4 also comprises two openings 6, 7 for holding two connecting wires 8, 9, and heating means 10 for heating the plate 3 to the operating temperature of the sensor, i.e. to about 600° C. or more. A cathode 1 and an anode 2, each made of an electronic but not ionic conductive material, are fixed on opposing faces of plate 3 and connected to the terminals of a D.C. voltage source (not represented) by means of connecting wires 8, 9.

Figure 6:
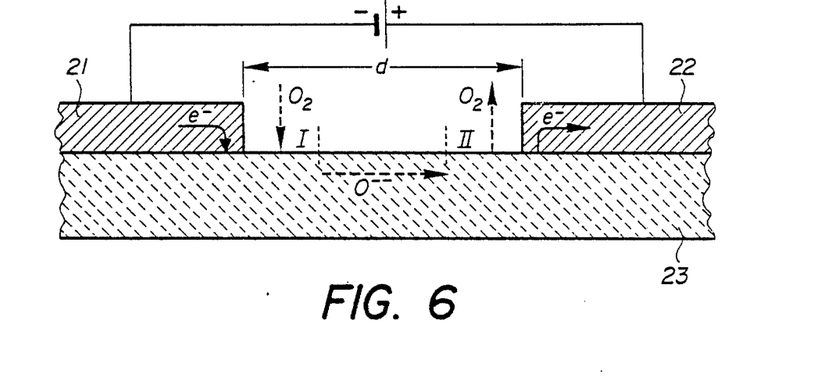
FIG. 6 shows a cross-section of an arrangement of electrodes located on the same side of the electrolytic slab.

Another embodiment of the device according to the invention is illustrated on FIG. 6. In this embodiment, numerals 21 and 22 designate a cathode and an anode, respectively. Numeral 23 designates a substrate made of solid electrolyte. This embodiment is constructed and operates according to the same criteria as the embodiment of FIGS. 1 and 2 although the cathode and the anode are located this time on the same side of the electrolyte slab; however, it should be remarked that here the resistance to the flow of $O^{--}$ ions in the electrolyte depends no longer only on the thickness of this slab but now on the distance between the electrodes 21 and 22. Actually, in this case, the thickness of the electrolyte becomes of relatively little significance. This distance "d" between the electrodes (from about 20 to 500 $\mu$m) should be such that the ionic resistance of the zirconia, at the operating temperature of the device, it is below $10^{-3}$ per each centimeter of the length of the cathode/electrolyte boundary line of zone I.

Figure 7:
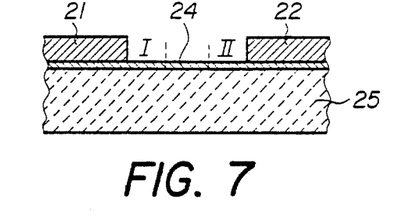
FIG. 7 shows the cross-section of an electrode arrangement involving a multilayer substrate.
Figure 8:
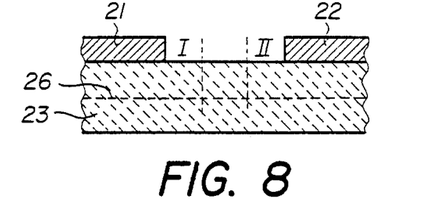
FIG. 8 shows the cross-section of an electrode arrangement having a heating means in the substrate.

This embodiment is advantageous in several respects. Indeed, since the thickness of the electrolyte body has little operative importance, it is possible to use a substrate 23 significantly thicker and mechanically stronger than in the embodiment of FIG. 1 without affecting the proper operation of the device; the latter is therefore less brittle. It is further possible to provide multilayer substrates (FIG. 7) if which only a top layer 24, that can be very thin since constituted by a high performance solid electrolyte such as for instance zirconia or scandium oxide, provides the necessary path to the $O^{--}$ ions, whereas a thicker layer 25 will provide mechanical resistance to the device. It is moreover possible, as illustrated in FIG. 8, to incorporate in substrate 23 a heating means 26, such as a heating resistor to be further described hereafter, in order to heat more rapidly the present device to its operating temperature.

Figures 9, 10:
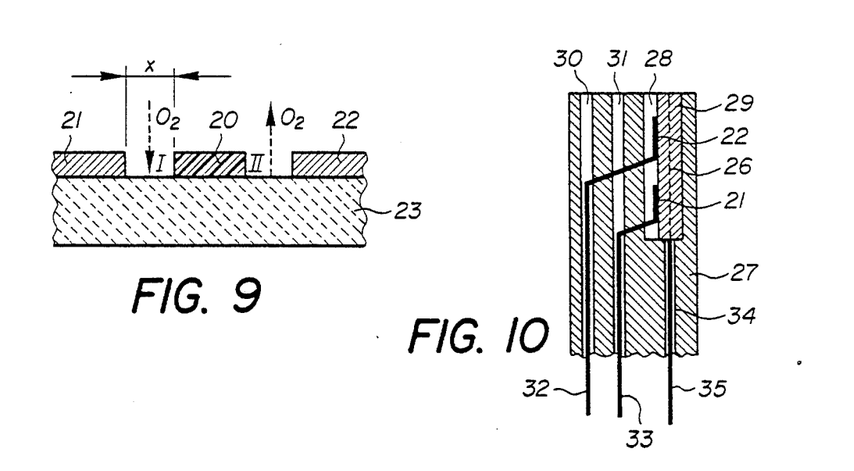
FIG. 9 shows the cross-section of a variant of FIG. 6 having a separating strip between the electrodes.
FIG. 10 shows the cross-section of a sensor derived from the principles shown in FIGS. 6 to 8.

FIG. 9 shows a variant of the embodiment of FIG. 6 in which a separating strip 20 made of electric insulator and gas tight material integral with plate 23 is placed in an intermediate middle position between electrodes 21 and 22. This strip will geometrically limit the width of zone I, (i.e. the cathode-electrolyte boundary region where $O_2 \rightarrow 2O^{-2}$; surface situated between strip 20 and cathode 21) by acting as a valve for limiting the rate of conversion of the molecular oxygen into $O^{--}$ ions. Indeed, as soon as the voltage applied between electrode 21 and 22 exceeds a certain limiting value, it will no longer control the current in zone I, whose effective area, i.e. its geometrical size between the cathode and the separating strip 20, becomes then operatively determinant. Obviously, this limiting value geometrically depends on the distance "x" for a given electrolyte. Naturally, the magnitude of the limiting value can be changed by changing the nature of the solid electrolyte, i.e. changing its ionic conductivity properties.

FIG. 10 represents an embodiment derived from the principles illustrated with reference to FIGS. 6 to 8. It comprises an insulating substrate 27 (ceramic) comporting a recess 28 containing a plate 29 made of a solid electrolyte with heating means 26 (see also FIG. 8), and two openings 30, 31 with connecting wires 32, 33 for connecting two electrodes 21 and 22, a cathode and an anode respectively, to the terminals of a D.C. source (not represented). An opening 34 of the body 27 enables to pass therethrough a connecting element 35 for connecting the heating means 26 to a source of power not represented in order to heat to the required temperature the electrolyte 29. When under use, the test gas is introduced into recess 28 for exposing thereto the electrodes 21, 22.

Figure 11:
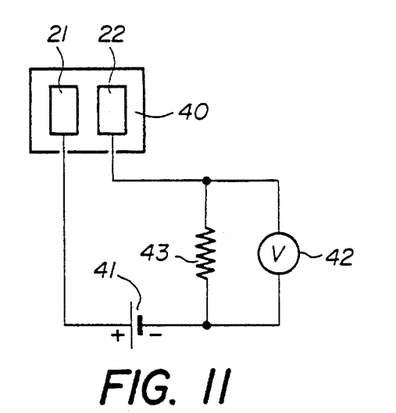
FIG. 11 schematically shows a probe having a sensor made of an anode connected to the positive terminal of an electric voltage source, a cathode connected to the negative terminal of the same source, and a resistor in parallel to a voltmeter.

FIG. 11 illustrates schematically a probe including a sensor 40 comprising an anode 21 connected to the positive terminal of an electric voltage source 41, for instance of 4 Volt. Another electrode 22, a cathode is connected to the negative terminal of the same source. The probe further comprises a voltmeter 42 connected in parallel to the ends of a resistor 49 itself connected in series in the electrode-electrolyte circuit. This voltmeter (of which the impedance is several orders of magnitude higher than that of the cell circuit enables to measure the intensity of the electric current circulating in the electrodes 21 and 22. It has been said that the voltage measured at the terminals of resistor 43 is a function of the oxygen content of the gas which is in contact with the sensor 40 and that this voltage can be made linearly dependent on this oxygen content by properly adjusting the geometry of the cell, the nature of the electrolyte and the operative conditions of the analysis.

Figure 12:
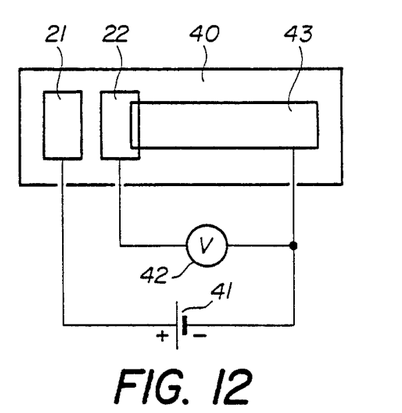
FIG. 12 shows an alternative to the embodiment of FIG. 11 in which the resistor is incorporated into the structure of the sensor.

It is of interest to also note that important function that resistor 43 can possibly have with regard to the relation which exists between the measured voltage and the temperature. It is known that the resistance of sensor 40 decreases when the temperature rises and consequently the difference of voltage applied between the electrodes decreases with the condition that the voltage provided by the source 41 and the value of the resistance of resistor 43 remain all constant. This effect can be minimized by adequately selecting the value for resistor 43 (see the examples); it can even be made practically zero if one selects a variable resistor 43 whose value increases with temperature with the proviso that the variation be near to that variation of the resistance of sensor 40 irrespective of the actual positive or negative sign thereof. Such correction of the effect of a temperature variation can for instance be achieved by incorporating resistor 43 to the structure of the sensor 40 as illustrated on FIG. 12 which discloses an installation for using the device according to the invention. Obviously, this last embodiment of an installation for the use of the device according to the invention can also properly operate even if the value of resistor 43 is independent of temperature.

In all the embodiments described above, the heating means 10, 26 can be of any nature and be constituted for instance by a simple electric resistor. The electrodes, can be made of metal such as silver, gold, platinum or a metal oxide. They can be applied on the solid electrolyte by any known technique such as CVD, PVD and silk-screen techniques for instance. The cathode is made of a fully dense non-porous material. This can be obtained from PVD thick layers or thick film metal pastes with powdered glass fired at about 850° C. The exact shape of the cathode can be obtained by screening techniques or by machining blocks of densified cathode material. Electroerosion and laser machining can be used for shaping the cathode.

The following examples illustrate the practical aspect of the invention.

EXAMPLE 1

A 4×4 mm chip of solid electrolyte made of $ZrO_2$ stabilized with 8 mole % of $Er_2O_3$ was machined by grinding to a thickness of a millimeter. The surface was coated with 2 microns of fully dense platinum by magnetron sputtering according to usual means. In order to provide an anode and a cathode from the Pt coating, a 4 mm long 300 micrometer wide groove was machind through the metal layer with a diamond wheel.

Platinum wires were connected to each electrode and an electric resistor (100 ohms) was placed in series with the two electrodes and a power source connected thereto. The chip was surrounded by an electric heating element and it was sealed in the opening of a gas sampling enclosure in a manner such that the electrodes and the groove therebetween are exposed to contact with samples of various mixtures of gas and oxygen. The mixtures contained 80% nitrogen and 20% of variable $O_2/CO_2$ composition. The test mixtures rated the following overall oxygen contents (% v/v): 0, 1, 2, 4 and 6%. The probe element was heated to 900° by means of its internal heating element, a voltage of 3 V (=5 V/cm of boundary line) was applied between the electrodes and the various mixtures were successively brought into contact with the chip. The voltage at the terminals of the resistor was measured with a high impedance voltmeter and the current was calculated from said voltage drop. The results are shown below:

| Oxygen content (% by vol.) | Voltage drop (mV) |
| --- | --- |
| 0 | 581 |
| 1 | 625 |
| 2 | 671 |
| 4 | 769 |
| 6 | 848 |

The above values plotted against each other provided a reasonably straight line with 44.3 mV/% oxygen. The ohmic resistance of the probe was equivalent to 600 ohms/cm. Unknown gas mixture in the above mentioned range were thereafter measurable with reference to the above calibration.

EXAMPLE 2

A chip like that of Example 1 was manufactured from $ZrO_2$ stabilized with 10 mole % of $Y_2O_3$. A conductive platinum layer was built up on one side of the chip by applying a coating of platinum paste containing glass powder (DEMETRON M-8005) and firing at 800° C. Then, a sinuated line (100 micrometers wide) was dug in the platinum layer from one edge thereof to the opposite one by means of a laser beam. The circonvoluted line (total length 4 cm therefore divided the platinum layer into two separate conductive areas (a cathode and an anode) providing, in between, a free electrolyte area (100 micrometers wide) which combined, in juxtaposition, zone I and zone II (see for example FIGS. 6 or 7) zone I being that near the cathode edge and zone II being that near to the anode edge). The chip was equipped and arranged as in the previous example and subjected at 800° C. to the same oxygen-gas compositions. The voltage was 2 V (0.5 V/cm of boundary line) and the internal resistance of the electrolyte (corresponding to ionization of $O_2$ into $O^{-2}$ ions, migration of the ions and release of oxygen at the anode) was 40 ohms/cm. The mV versus oxygen concentration are shown below:

| Oxygen content (%) | Voltage drop (m/V) |
| --- | --- |
| 1 | 902 |
| 2 | 932 |
| 4 | 970 |
| 6 | 1010 |

EXAMPLE 3

A chip identical with that of example 1 was used. Two 400 micrometers separated, 4 mm long straight slots were dug into one side of the chip (slightly over 100 micrometer wide) and 100 micrometer diameter platinum wires were inserted into the slots to provide a cathode and an anode. The wires were connected to a DC power source (2 Volts =5 v/cm, series resistor 10 ohms) and the chip was subjected, at a temperature of 900°, to various oxygen-gas mixtures. The ohmic losses were 62.5 ohms/cm of cathode boundary and the sensitivity about 15 mV/% oxygen. Results are shown below:

| Oxygen content (%) | Voltage drop (mV) |
| --- | --- |
| 0 | 50 |
| 1 | 77 |
| 2 | 98 |
| 4 | 123 |
| 6 | 142 |

Using a voltage on only 0.6 V/cm provided an internal resistance of 60 ohms/cm but less functional linearity.

EXAMPLE 4

A in the previous example, a chip was used made of $ZrO_2$ stabilized with 10% $Y_2O_3$ (4×20 mm; 0.3 mm thick). One side was coated with platinum paste (DEMETRON M-80005) and fired at 900° to leave open some porosity (pore size about 10 micrometers). Indeed, if the firing temperature is kept at relatively moderate temperature, a residual porosity (due to the presence of the micro glass beads) remains in the layer; at higher tempertures, coalescence occurs with formation of a fully densified, non-porous conductive layer with macroholes therein. Half of the other side of the chip was coated with a fully dense layer of platinum (cathode) as in example 1 (4×10 mm; 20 micrometer thick). The chip was equipped with an internal electric heater means and was subjected, on the cathode side to testing gas mixtures, at 700° C., as in the previous example (load resistor 100 ohms; voltage 2 volts). The set-up was like that represented on FIG. 2. The results are shown below; the sensitivity was about 52 mV/% $O_2$. The voltage was 5 volts/cm of cathode-electrolyte boundary perimeter and the ohmic losses were 80 ohms/cm.

| Oxygen content (%) | Voltage drop (mV) |
| --- | --- |
| 1 | 460 |
| 2,5 | 495 |
| 4,5 | 730 |
| 6,6 | 850 |

EXAMPLE 5

A chip as in example 4 was selected; it was coated on both sides with a DEMETRON 1308-A paste but the first side was densified at 1400° C. which provided a non-porous densified conductive platinum layer with macro-openings of about 100 micrometer size (cathode). The other side was fired at 900° C. to get porosity of less than 10 micrometers (anode). Two volts were applied with a load of 10 ohms. The evaluated cathode-electrode boundary perimeter (the sum of the holes in the cathode) was about 6 cm for a cathode coating of 4×4 mm. The voltage is therefore 2/6=0.33 volts/cm of boundary line. This embodiment shows how the present probe can be minaturized by using a cathode of very small overall surface although with a relatively large cathode-electrolyte boundary perimeter. This results in higher sensitivities, about 195 mV/% $O_2$ in this case. The ohmic loss was about 60 ohms/cm. The results are listed below:

| Oxygen content (%) | Voltage drop (mV) |
| --- | --- |
| 0 | 300 |
| 1 | 490 |
| 2 | 620 |
| 4 | 1020 |

I claim:

1. A dry electrolytic cell sensor for determining the oxygen content of a sample gas without the use of a reference gas, the sensor comprising:
   (a) first electrode means acting as an anode, for the conversion of $O^{--}$ ions to $O_2$ gas, said anode being formed from a porous electroconductive material which is not conductive of ions;
   (b) second electrode means, acting as a cathode, for the conversion of $O_2$ to $O^{--}$ ions, said cathode being formed from a nonporous electroconductive material which is not conductive of ions;
   (c) solid electrolyte means for conducting $O^{--}$ ions between said anode and said cathode, the electrolyte separating said electrode means and being impervious to the passage of $O_2$, and the electrodes being positioned in electronic contact with the electrolyte;
   (d) power means for applying a DC voltage across said electrode means;
   wherein the anode and cathode are positioned on opposite facing sides of the electrolyte, and said electrolyte is from 50 to 500 μm in thickness;
   wherein the nonporous cathode material is shaped so as to expose said electrolyte directly to a sample gas, an area of sample gas/electrolyte contact being defined by a cathode/electrolyte junction boundary line;
   wherein the ionic resistance of said electrolyte is not greater than $10^3$ ohm/cm of said cathode/electrolyte junction boundary line;
   wherein the voltage applied by said power means is from 0.2 to 12 volts/cm of said cathode electrolyte junction boundary line;
   and wherein the electrolyte is heated to a temperature such that the internal resistance of the electrolyte to the flow of $O^{--}$ ions is about a tenth or less than the resistance associated with $O_2$ ionization,
   so that the current flowing across the electrode means of the sensor is controlled by the rate of ionization of said $O_2$ gas at the cathode area of contact.

2. A sensor as in claim 1 wherein said electrolyte comprises stabilized $ZrO_2$ having a thickness of from 100-300 μm.

3. A dry electrolytic cell sensor for determining the oxygen content of a sample gas without the use of a reference gas, the sensor comprising:
   (a) first electrode means acting as an anode, for the conversion of $O^{--}$ ions to $O_2$ gas, said anode being formed from a porous electroconductive material which is not conductive of ions;
   (b) second electrode means, acting as a cathode, for the conversion of $O_2$ to $O^{--}$ ions, said cathode being formed from a nonporous electroconductive material which is not conductive of ions;
   (c) solid electrolyte means for conducting $O^{--}$ ions between said anode and said cathode, the electrolyte separating said electrode means and being impervious to the passage of $O_2$, and the electrodes being positioned in electronic contact with the electrolyte;
   (d) power means for applying a DC voltage across said electrode means;
   wherein said anode and cathode are arranged on the same side of said electrolyte, separated by a distance of from 20-500 μm;
   wherein the nonporous cathode material is shaped so as to expose said electrolyte directly to a sample gas, an area of sample gas/electrolyte contact being defined by a cathode/electrolyte junction boundary line;
   wherein the ionic resistnce of said electrolyte is not greater than $10^3$ ohm/cm of said cathode/electrolyte junction boundary line;
   wherein the voltage applied by said power means is from 0.2 to 12 volts/cm of said cathode electrolyte junction boundary line;
   and wherein the electrolyte is heated to a temperature such that the internal resistance of the electrolyte to the flow of $O^{--}$ ions is about a tenth or less than the resistance associated with $O_2$ ionization,
   so that the current flowing across the electrode means of the sensor is controlled by the rate of ionization of said $O_2$ gas at the cathode area of contact.

4. A sensor as in claim 3 wherein said anode and cathode are separated by a distance of from 50-100 $\mu m$.

5. A sensor as in claim 3 wherein an insulating strip is positioned on the surface of said electrolyte between said anode and said cathode, at a distance from each of between 1 and 10 $\mu m$.

6. A dry electrolytic cell sensor for determining the oxygen content of a sample gas without the use of a reference gas, the sensor comprising:
   (a) first electrode means acting as an anode, for the conversion of $O^{--}$ ions $O_2$ gas, said anode being formed from a porous electroconductive material which is not conductive of ions;
   (b) second electrode means, acting as a cathode, for the conversion of $O_2$ to $O^{--}$ ions, said cathode being formed from a nonporous electroconductive material which is not conductive of ions;
   (c) solid electrolyte means for conducting $O^{--}$ ions between said anode and said cathode, the electrolyte separating said electrode means and being impervious to the passive of $O_2$, and the electrodes being positioned in electronic contact with the electrolyte;
   (d) power means for applying a DC voltage across said electrode means;
   wherein openings which make up the area of sample gas/electrolyte contact at the cathode are of a size about one order of magnitude greater than the size of the pores in the anode;
   wherein the nonporous cathode material is shaped so as to expose said electrolyte directly to a sample gas, an area of sample gas/electrolyte contact being defined by a cathode/electrolyte junction boundary line;
   wherein the ionic resistance of said electrolyte is not greater than $10^3$ ohm/cm of said cathode/electrolyte junction boundary line;
   wherein the voltage applied by said power means is from 0.2 to 12 volts/cm of said cathode electrolyte junction boundary line;
   and wherein the electrolyte is heated to a temperature such that the internal resistance of the electrolyte to the flow of $O^{--}$ ions is about a tenth or less than the resistance associated with $O_2$ ionization,
   so that the current flowing across the electrode means of the sensor is controlled by the rate of ionization of said $O_2$ gas at the cathode area of contact.

7. A sensor as in claim 6 wherein the opening at the cathode are at least 100 $\mu m$ in diameter and the pores in said anode are 10 $\mu m$ or less.

8. A dry electrolyte cell sensor for determining the oxygen content of a sample gas without the use of a reference gas, the sensor comprising:
   (a) first electrode means acting as an anode, for the conversion of $O^{--}$ ions to $O_2$ gas, said anode being formed from a porous electroconductive material which is not conductive of ions;
   (b) second electrode means, acting as a cathode, for the conversion of $O_2$ to $O^{--}$ ions, said cathode being formed from a nonporous electroconductive material which is not conductive of ions;
   (c) solid electrolyte means for conducting $O^{--}$ ions between said anode and said cathode, the electrolyte separating said electrode means and being impervious to the passage of $O_2$, and the electrodes being positioned in electronic contact with the electrolyte;
   (d) power means for applying a DC voltage across said electrode means;
   (e) means for measuring the intensity of an electrical signal representative of the oxygen content of a sample gas comprising a resistance connected in series between the cathode and the voltage source and a voltmeter connected in parallel with said resistance;
   wherein the nonporous cathode material is shaped so as to expose said electrolyte directly to a sample gas, an area of sample gas/electrolyte contact being defined by a cathode/electrolyte junction boundary line;
   wherein the ionic resistance of said electrolyte is not greater than $10^3$ ohm/cm of said cathode/electrolyte junction boundary line;
   wherein the voltge applied by said power means is from 0.2 to 12 volts/cm of said cathode electrolyte junction boundary line;
   and wherein the electrolyte is heated to a temperature such that the internal resistance of the electrolyte to the flow of $O^{--}$ ions is about a tenth or less than the resistance associated with $O_2$ ionization,
   so that the current flowing across the electrode means, of the sensor is controlled by the rate of ionization of said $O_2$ gas at the cathode area of contact.

9. A sensor as in claim 8 wherein the cathode is an electrically conductive film coated on an electrolyte supporting member.

* * * * *